United States Patent [19]

Mutai et al.

[11] 4,187,321

[45] Feb. 5, 1980

[54] METHOD FOR PRODUCING FOODS AND DRINKS CONTAINING BIFIDOBACTERIA

[75] Inventors: Masahiko Mutai, Higashi Yamato; Mitsuo Mada, Kodaira; Kiyohiro Shimada, Kunitachi, all of Japan

[73] Assignee: Kabushiki Kaisha Yakult Honsha, Tokyo, Japan

[21] Appl. No.: 861,002

[22] Filed: Dec. 15, 1977

[30] Foreign Application Priority Data

Mar. 31, 1977 [JP] Japan .................................. 52-37008

[51] Int. Cl.$^2$ .................................................. A23C 9/12
[52] U.S. Cl. ..................................................... 426/43
[58] Field of Search ............................. 426/34, 42, 43

[56] References Cited

U.S. PATENT DOCUMENTS

| | | | |
|---|---|---|---|
| 3,480,443 | 11/1969 | Schuler et al. ........................ | 426/43 |
| 4,087,559 | 5/1978 | Mutai et al. ........................... | 426/43 |
| 4,091,117 | 5/1978 | Mutai et al. ........................... | 426/43 |

FOREIGN PATENT DOCUMENTS 2421084  11/1975  Fed. Rep. of Germany ............ 426/34

*Primary Examiner*—David M. Naff
*Attorney, Agent, or Firm*—Wenderoth, Lind & Ponack

[57] ABSTRACT

Foods and drinks containing bifidobacteria are prepared by growing in a milk medium under aerobic conditions a mixture of bifidobacteria containing a mutant strain of oxygen-resistant Bifidobacterium and a strain of obligatory anaerobic Bifidobacterium. Presence of the oxygen-resistant strain enables growing the obligatory anaerobic strain under aerobic conditions in a pure milk medium without added growth promoting substances.

2 Claims, No Drawings

METHOD FOR PRODUCING FOODS AND DRINKS CONTAINING BIFIDOBACTERIA

DETAILED EXPLANATION OF THE INVENTION

This invention concerns improvement of the methods for cultivating Bifidobacterium inoculated into milk media or semi-synthetic media and for processing the resultant cultures suitably to manufacture food and drink containing the above-mentioned bacteria.

Bifidobacterium is known well as the bacteria representing almost all of the intestinal flora of suckling infants. There are many reports on the study of the physiological significance of this bacteria, clarifying the inhibitory effect on putrefaction by putrefactive bacteria, the inhibitory effect on production of toxic amines, the digestive effect on human milk casein by the effect of phosphoprotein phosphatase, and the inhibitory effect on growth of pathogens by a decreased intestinal pH following production of organic acids resulting from lactose, such as lactic acid, acetic acid, and formic acid. However, this useful Bifidobacterium is present in a very small amount in the intestines of bottle fed infants, which is considered to be one of the causes for their liability to intestinal diseases, greater than that of suckling infants.

Aimed at approximating the intestinal flora of suckling infants, an attempt has been made to manufacture Bifidobacterium-containing powdered milk for infants and, further, to manufacture fermentative dairy products by use of various species of Bifidobacterium from which a healthful effect on children other than infants and on adults is expected. However, (a) Bifidobacterium is originally obligatorily anaerobic, requiring strict anaerobic conditions for growth;

(b) it grows very poorly on pure cow's milk media containing no growth accelerant such as yeast extract or corn steep liquor (CSL); and (c) when growth accelerants and reductants are added to cow's milk media, it grows under the same aerobic conditions as those for cultivation of lactobacilli, but those additives are generally expensive and spoil the taste of the resultant cultures.

Since the cultivation is much more difficult than that of lactobacilli due to the above reasons, industrial production of food and drink containing the bacteria has not yet been made.

In view of the above fact, the present inventors have been performing many studies aimed at establishing a method for practical cultivation of Bifidobacterium to provide food and drink containing it at a low price.

In the process, we found *Bifidobacterium bifidum*, YIT-4002 (FERM-P No. 3371) and YIT-4005 (FERM-P No. 3372) and *Bifidobacterium breve*, YIT-4006 (FERM-P No. 3906), which are mutant strains (dissocians) of Bifidobacterium with highly specific properties, and applied for a patent for the invention of a method for manufacturing fermentative dairy products. The above mutant strains (dissociants) can multiply under aerobic conditions in pure cow's milk media and above all, YIT-4005 is so strongly acid-resistant that they do not die easily during preservation. As a result of further study, we have obtained the following interesting data. When the mutant strains (dissociants) are cultivated with ordinary obligatory anaerobic bifidobacteria, the obligatory anaerobes grow satisfactorily in a pure cow's milk medium under aerobic conditions (see the experimental cases described later).

Being completed based on the above data, the present invention is characterized by a mixed cultivation of oxygen-resistant mutant strains (dissociants) of Bifidobacterium with obligatory anaerobic bifidobacteria in manufacturing food and drink containing the above-mentioned bacteria by cultivating obligatory anaerobic bifidobacteria in a milk or semi-synthetic medium and processing the resultant culture suitably.

Based on this invention, food and drink containing more than one species of bifidobacterium can be obtained by simple cultivation of Bifidobacterium, which is an obligatory anaerobe, under aerobic conditions similar to those for oxygen-resistant mutant strains or lactobacilli. This method is more advantageous than the one using ordinary Bifidobacterium or its oxygen-resistant mutant strains alone since it can provide products collectively excellent in physiological activity and taste by combining the species most suitable according to the type of product and the purpose of use, selected from among the species of Bifidobacterium with different properties in physiological activity, acid-producing ability during cultivation, and effect on the taste of the product.

The oxygen-resistant mutant strains of Bifidobacterium used in the procedures of this invention refer to all of the mutant strains of Bifidobacterium possible to grow in pure milk media under aerobic conditions, such as the above-mentioned YIT-4002, YIT-4005, and YIT-4006. The growth promoting activity of obligatory anaerobic strains under aerobic conditions is common to all oxygen-resistant mutant strains and is not limited to the above 3 species.

No restriction is imposed on the composition of the media used for the mixed cultivation of obligatory anaerobic strains and oxygen-resistant mutant strains, nor is any special ingredient required. For example, any milk with a concentration of from 10% to 20% of milk solid content (whole milk, skim milk, or reduced milk reconstituted from their powdered milks) can be used. Semi-synthetic media containing no milk solid can also be used. Since growth promoting agents such as yeast extract, CSL, and peptone and reductants such as L-ascorbic acid and L-cysteine are not necessary, fermented milk containing Bifidobacterium alone with no additives is obtained. However, growth of the bacteria may be promoted by use of the above additives within the limits in which their effect on the taste of products is permissible, or when there is no problem in view of the characters of products.

For the starter, preparations of obligatory anaerobic strains and oxygen-resistant mutant strains are mixed 1:1–3:1 for inoculation of 1–3 weight % into media. It is not necessary to make the medium anaerobic during cultivation, allowing the use of apparatuses similar to those used routinely for cultivation of lactobacilli.

Cultivation at 37° C. yields the maximum viable count for each strains usually in 18–24 hours. Organic acids such as lactic acid and acetic acid are formed during the growth. When cultivation is further continued, the bacterial count begins to decrease, but acid formation continues, reaching saturation in 40–50 hours. Monitoring the cultivation process, cultivation is discontinued at an appropriate time according to the purpose of use of the culture.

The resultant culture may be used as it is for food containing Bifidobacterium, or the concentration and taste of the culture may be conditioned by the addition of sweetening materials, fruit juice, water, and flavors, etc. In addition, the culture may be dried to obtain food or preparations in powder or tablet form containing Bifidobacterium. No restriction is placed on the means to process the culture, or on the type of final products as long as they do not kill the Bifidobacterium. The "food and drink" referred to in this invention includes all which is ingested ranging from food and drink for taste to preparations for preventive medicines.

This invention is explained below with an experiment and examples, and a full account is given of representative bacteriological properties of the 3 aforementioned species of oxygen-resistant mutants. The "acidity" is the volume in ml of 0.1 N sodium hydroxide solution required to neutralize 10 ml of culture solution.

Experiment

Into a 300 ml flask, 150 ml of 16% reconstituted skim milk was pipetted, and a cotton stopper was applied, followed by sterilization at 120° C. for 15 minutes. After the medium was cooled to 37° C. by stirring in running water, 2 weight % of each starter of Bifidobacterium given in Table 1 was inoculated for static culture at 37° C. In the meanwhile, time-course changes of the viable count and acidity were measured. The results are shown in Table 1. (The aerobic conditions referred to in this invention indicate the above-mentioned cultural conditions. The cultural conditions were the same as the basic cultural conditions for the so-called dairy lactobacilli used for the manufacture of fermented milk, cheese, and drink containing lactic acid bacteria).

YIT-4002, YIT-4005, and YIT-4006, oxygen-resistant mutant strains of Bifidobacterium, all grew excellently in cow's milk media under aerobic conditions, giving a viable count of $2.3-5.0 \times 10^9$/ml after 17 hours of culture. On the contrary, the other strains of Bifidobacterium (all were the standard, obligatory anaerobic strains) showed hardly any increase in viable count; some showed a remarkably slow increase in acidity and died rapidly after inoculation.

Into the medium prepared by the same method as that mentioned above, 2 weight % of the starter obtained by mixing equal volumes of each species of Bifidobacterium given in Table 2 and one of the above-mentioned mutant strains was inoculated for static culture at 37° C., during which the viable count and acidity were measured with the lapse of time. The results are shown in Table 2.

When the mixture of Bifidobacterium and the above-mentioned mutant strains was cultivated, the viable count and acidity of Bifidobacterium increased similarly to those of the above-mentioned mutant strains even in a pure milk medium under aerobic conditions, though there were some differences according to species.

Table 1

| cultivation hours | 0 | | 17 | | 24 | | 41 | |
|---|---|---|---|---|---|---|---|---|
| measurement items / strains | acidity | viable count/ml | acidity | viable count/ml | acidity | viable count/ml | acidity | viable count/ml |
| YIT-4002 | 3.5 | $4.2 \times 10^7$ | 14.4 | $4.9 \times 10^9$ | 21.2 | $4.8 \times 10^9$ | 27.2 | $7.3 \times 10^8$ |
| YIT-4006 | 3.4 | $7.0 \times 10^7$ | 10.0 | $2.3 \times 10^9$ | 13.5 | $8.9 \times 10^8$ | 17.0 | $5.6 \times 10^8$ |
| YIT-4005 | 3.5 | $4.5 \times 10^7$ | 13.9 | $5.0 \times 10^9$ | 19.6 | $4.6 \times 10^9$ | 25.1 | $3.1 \times 10^9$ |
| B. longum | 3.6 | $5.7 \times 10^7$ | 5.2 | $6.2 \times 10^7$ | 5.4 | $5.4 \times 10^7$ | 6.3 | $1.0 \times 10^7$ |
| B. breve | 3.6 | $4.0 \times 10^7$ | 6.7 | $5.1 \times 10^7$ | 7.8 | $3.6 \times 10^7$ | 9.2 | $1.1 \times 10^7$ |
| B. adolescentis | 3.4 | $3.4 \times 10^7$ | 4.4 | $1.8 \times 10^7$ | 4.6 | $1.2 \times 10^7$ | 5.1 | $6.4 \times 10^6$ |
| B. infantis | 3.5 | $6.0 \times 10^7$ | 4.5 | $4.6 \times 10^6$ | 4.8 | $1.2 \times 10^6$ | 5.3 | $1.0 \times 10^5$ |
| B. bifidum | 3.4 | $4.0 \times 10^7$ | 5.9 | $6.0 \times 10^7$ | 6.6 | $3.9 \times 10^7$ | 7.5 | $2.4 \times 10^7$ |

Table 2

| cultivation hours | 0 | | 17 | | 24 | | 41 | |
|---|---|---|---|---|---|---|---|---|
| measurement items / strains | acidity | viable count/ml | acidity | viable count/ml | acidity | viable count/ml | acidity | viable count/ml |
| B. longum | | $2.5 \times 10^7$ | | $7.7 \times 10^8$ | | $9.2 \times 10^8$ | | $1.8 \times 10^8$ |
| YIT-4002 | | $2.2 \times 10^7$ | | $4.7 \times 10^9$ | | $5.8 \times 10^9$ | | $4.2 \times 10^8$ |
| Total | 3.5 | $4.6 \times 10^7$ | 13.9 | $5.5 \times 10^9$ | 22.8 | $6.8 \times 10^9$ | 28.6 | $6.5 \times 10^8$ |
| B. breve | | $7.7 \times 10^7$ | | $6.5 \times 10^9$ | | $4.8 \times 10^9$ | | $3.4 \times 10^7$ |
| YIT-4002 | | $2.0 \times 10^7$ | | $2.0 \times 10^9$ | | $1.4 \times 10^9$ | | $3.8 \times 10^6$ |
| Total | 3.6 | $9.6 \times 10^7$ | 18.5 | $8.5 \times 10^9$ | 24.5 | $6.5 \times 10^9$ | 29.5 | $3.7 \times 10^7$ |
| B. adolescentis | | $1.7 \times 10^7$ | | $4.0 \times 10^8$ | | $8.9 \times 10^8$ | | $5.6 \times 10^8$ |
| YIT-4005 | | $2.7 \times 10^7$ | | $5.6 \times 10^9$ | | $4.9 \times 10^9$ | | $3.5 \times 10^9$ |
| Total | 3.4 | $4.2 \times 10^7$ | 13.4 | $6.5 \times 10^9$ | 21.0 | $5.9 \times 10^9$ | 28.4 | $4.2 \times 10^9$ |
| B. infantis | | $3.8 \times 10^7$ | | $8.5 \times 10^8$ | | $1.2 \times 10^9$ | | $6.5 \times 10^8$ |
| YIT-4005 | | $2.8 \times 10^7$ | | $3.7 \times 10^9$ | | $6.0 \times 10^9$ | | $3.8 \times 10^9$ |
| Total | 3.5 | $6.2 \times 10^7$ | 11.8 | $4.5 \times 10^9$ | 22.3 | $7.0 \times 10^9$ | 28.9 | $4.5 \times 10^9$ |
| B. bifidum | | $2.5 \times 10^7$ | | $4.6 \times 10^9$ | | $5.2 \times 10^9$ | | $4.0 \times 10^8$ |
| YIT-4005 | | $3.0 \times 10^7$ | | $3.0 \times 10^9$ | | $3.5 \times 10^9$ | | $1.3 \times 10^9$ |
| Total | 3.4 | $5.6 \times 10^7$ | 17.9 | $6.8 \times 10^9$ | 25.6 | $7.8 \times 10^9$ | 31.6 | $1.5 \times 10^9$ |
| B. longum | | $4.4 \times 10^7$ | | $5.9 \times 10^8$ | | $8.0 \times 10^8$ | | $2.1 \times 10^8$ |
| YIT-4006 | | $4.2 \times 10^7$ | | $2.5 \times 10^9$ | | $1.6 \times 10^9$ | | $4.0 \times 10^8$ |
| Total | 3.4 | $6.0 \times 10^7$ | 12.8 | $2.7 \times 10^9$ | 23.0 | $1.8 \times 10^9$ | 28.0 | $4.3 \times 10^8$ |

EXAMPLE 1

Into a 16% whole fat milk medium, 1% each of the starters of *Bifidobacterium longum* (I) and *Bifidobacterium bifidum* (YIT-4002) (II) was inoculated for cultivation under aerobic conditions at 37° C. for 30 hours. The viable count of the resultant culture was a total count of $2.5 \times 10^9$/ml ($6.5 \times 10^8$/ml for I and $2.0 \times 10^9$/ml of II), and the acidity was 24.5. The culture was homogenized through a homogenizer, and 110 parts of the culture were mixed with 3 parts of sucrose, 3 parts of sorbitol, 3 parts of carrot juice, and 80 parts of water to obtain a fermented milk product containing the 2 above-mentioned species.

EXAMPLE 2

Into a 10% skim milk medium, 1% each of the starters of *Bifidobacterium bifidium* (III) and *Bifidobacterium breve* (YIT-4006) (IV) was inoculated for cultivation under aerobic conditions at 37° C. for 20 hours. The viable count of the resultant culture was a total count of $2.5 \times 10^9$/ml ($1.4 \times 10^9$/ml for III and $1.9 \times 10^9$/ml for IV). The culture was frozen, as it was, and was dried under a reduced pressure of below 2 mmHg for about 6 hours to obtain a dried powder of a fermented milk product containing the 2 above-mentioned species.

EXAMPLE 3

Into the semi-synthetic medium of the following composition, 1.0% each of the starters of *Bifidobacterium longum* (V), *Bifidobacterium bifidum* (YIT-4005) (VI), and *Lactobacillus acidophilus* (VII) was inoculated for aerobic culture at 37° C. for 20 hours. The viable count of the resultant culture was a total count of $3.6 \times 10^9$/ml ($4.0 \times 10^8$/ml for V, $1.0 \times 10^9$/ml for VI, and $1.7 \times 10^9$ml for VII). The culture was introduced into a freeze centrifuge for separation and collection of cells from the culture. The cells were dispersed in 30 ml of a medium containing skim milk (10%), sodium glutamate (1.0%), and Vitamin C (1%) and were freeze-dried to obtain a dried material containing the above 3 species. The resultant dried material was mixed with a 20-fold volume of dried starch and was made into tablets with a tabletting machine.

| Composition of Medium | |
|---|---|
| Treated CSL* | 70 g |
| Glucose | 20 g |
| KH$_2$PO$_4$ | 1 g |
| K$_2$HPO$_4$ | 2 g |
| Water | 927 ml |
| (pH 7.0) | |

*After citric acid was dissolved in CSL at 10%, the pH was adjusted to 8.0 with sodium hydroxide. Centrifugation was carried out at 10,000 rpm for 10 minutes to eliminate the precipitate.

Bacteriological Properties of the Oxygen-Resistant Mutant Strains of Bifidobacterium (1) Taxological Properties They are Gram-positive asporogenic (non-spore forming) bacilli with granules having an affinity for methylene blue in the cell. Under a microscope, they are short clavate bacilli which often bifurcate. The colonies are cylindrical, convex, or lenticular. When cultivated in 12% reduced skim milk, they produce mainly acetic acid and lactic acid.

Catalase (−), milk coagulability (+), liquefaction of gelatin (−), production of hydrogen sulfide (−), indole production (−), reduction of nitric acid (−), production of carbon dioxide (−).

(2) Fermentation of Sugar (a) YIT-4002, YIT-4005

Positive for glucose, fructose, lactose, and galactose. Negative for arabinose, xylose, salicin, mannose, mannitol, melezitose, cellobiose, sorbitol, inulin, trehalose, rhamnose, maltose, ribose, and sorbose.

(b) YIT-4006

Positive for glucose, fructose, lactose, galactose, salicin, melezitose, cellobiose, maltose, ribose, and mannose, and negative for arabinose, xylose, mannitol, sorbitol, inulin, trehalose, rhamnose, and sorbose.

(3) Growth Conditions (a) YIT-4002, YIT-4005

25°–45° C., pH 5–7 (optimum conditions, 36°–38° C., pH 6–7).

(b) YIT-4006

25°–42° C., pH 5–9 (optimum conditions 36°–38° C., pH 6–7).

Based on the above properties, (a) YIT-4002 and YIT-4005 and (b) YIT-4006 were identified to be (a) *Bifidobacterium bifidum* and (b) *Bifidobacterium breve* on reference to the classification in Bargey's manual (1974). However, since they had the aforementioned properties that are not possessed by the known species of Bifidobacterium, we judged that they were mutant strains of Bifidobacterium.

What we claim is:

1. A method for producing foods and drinks containing at least two kinds of viable bifidobacteria, which comprises adding to a milk medium a bifidobacteria mixture containing at least one oxygen-resistant mutant strain of Bifidobacterium selected form the group consisting of *Bifodobacterium bifidum* YIt-4002, Deposit No. FERM-P 3371, *Bifidobacterium bifidum* YIT-4005, Deposit No. FERM-P 3372 and *Bifidobacterium breve* YIT-4006, Deposit No. FERM-P 3906, and at least one strain of obligatory anaerobic Bifidobacterium selected from the group consisting of *Bifidobacterium longum*, *Bifidobacterium breve*, *Bifidobacterium adolescentis*, *Bifidobacterium infantis* and *Bifidobacterium bifidum*, and growing the bifidobacteria mixture in the milk medium under aerobic conditions in the absence of added growth promoting substances normally necessary for the obligatory anaerobic Bifidobacterium alone to grow under aerobic conditions in a pure milk medium.

2. A method for producing foods and drinks containing at least two kinds of viable bifidobacteria according to claim 1, wherein strains of Lactobacillus are additionally added to said milk medium.

* * * * *